United States Patent [19]

Pietsch et al.

[11] 4,009,161

[45] Feb. 22, 1977

[54] 6-METHYL-2H-1,3-OXAZIN-2,4(3H)DIONE-3-SULFOHALIDES

[75] Inventors: Hartmut Pietsch, Hofheim, Taunus; Karl Clauss, Rossert, Taunus; Erwin Schmidt, Kelkheim, Taunus; Harald Jensen, Frankfurt am Main, all of Germany

[73] Assignee: Hoechst Aktiengesellschaft, Frankfurt am Main, Germany

[22] Filed: July 16, 1975

[21] Appl. No.: 596,227

[30] Foreign Application Priority Data

July 18, 1974 Germany .......................... 2434563

[52] U.S. Cl. ............................................ 260/244 R
[51] Int. Cl.[2] .......... C07D 265/100; C07D 273/00; C07D 295/00
[58] Field of Search ................................ 260/244 R

[56] References Cited

UNITED STATES PATENTS 3,394,132    7/1968    Martin et al. ..................... 260/244

OTHER PUBLICATIONS

*Derwent Report*—(70/31,663; 70/37,018 — Abstracts of Japanese Specifications).

Primary Examiner—Frederick E. Waddell
Attorney, Agent, or Firm—Curtis, Morris & Safford

[57] ABSTRACT

3-Sulfohalides of 6-methyl-2H-1,3-oxazin-2,4(3H)-dione of the formula I

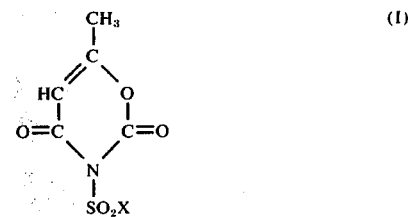

in which X represents fluorine or chlorine are prepared by reacting fluorosulfonyl isocyanate or chlorosulfonyl isocyanate, at a temperature of from −35° to +70° C, optionally in the presence of an inert solvent, with diketene, acetoacetyl fluoride, acetoacetyl chloride, acetoacetic acid or an isopropenyl ester of the formula $CH_2=C(OOCR)-CH_3$ in which R represents an alkyl radical having from 1 to 4 carbon atoms, a substituted or unsubstituted phenyl or benzyl radical.

3 Claims, No Drawings

6-METHYL-2H-1,3-OXAZIN-2,4(3H)DIONE-3-SULFOHALIDES

This invention relates to 3-sulfohalides of 6-methyl-2H-1,3-oxazin-2,4(3H)-dione of the formula I

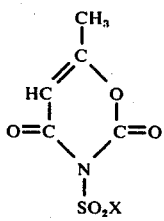

in which X represents fluorine or chlorine.

Compounds of the following formula II

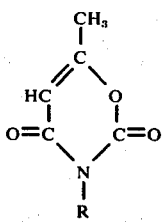

in which R represents an unsubstituted or substituted alkyl or aryl group are known. Compounds of this type are obtained by reacting corresponding isocyanates with diketene in an inert solvent, for example toluene in the presence of an acid catalyst at a temperature in the range of from 110° to 115° C. A reaction time of several hours is required (cf. Japanese Specifications 69/12,735, 70/31,663 and 70/37,018 Derwent Report).

It has also been proposed to transform 3-substituted 2-alkyl- or 2-aryl-imino-6-methyl-2H-1,3-oxazin-4(3H)-one, prepared from symmetrical S-methyl-isothioureas and diketene in boiling benzene, by heating with aqueous hydrochloric acid into compounds of formula II (cf. J. Chem. Soc. (1954) page 845; Tetrahydron Letters 1966, page 3231).

3-Alkyl-substituted compounds of formula II can also be prepared by reacting alkyl-carbamic acid morpholides with diketene in boiling glacial acetic acid (Khim. Geterots.Soedin, (1967) page 48) or by treating N-acetoacetyl-carbamic acid esters with concentrated sulfuric acid or boiling trifluoroacetic acid (Tetrahydron letters 1966, page 3231).

It is further known to prepare compounds of formula II from corresponding substituted 1,3-dioxin-4-ones and alkyl or aryl iso-cyanates which may be substituted, at a temperature of from 80° to 200° C, optionally in the presence of an inert solvent (cf. German Offenlegungsschrift No. 2,005,118).

The aforesaid processes are, however, unsuitable for the synthesis of the novel compounds of formula I. The diketene-isocyanate method as well as the dioxinone-isocyanate method cannot be used because of the high reaction temperatures, since the compounds carrying a halogenosulfonyl substituent at the nitrogen atom of the ring are thermally little stable and decompose vividly at temperatures below 100° C. On the other hand, the compounds are very sensitive to solvolysis so that the methods carried out in aqueous acid solutions or glacial acetic acid cannot be used either.

It is therefore a further object of the present invention to provide a process for the manufacture of a compound of formula I, which comprises reacting at a temperature in the range of from −35° to +70° C, preferably in the presence of an inert solvent, fluorosulfonyl isocyanate (hereinafter designated FSI) or chlorosulfonyl isocyanate (hereinafter designated CSI) with diketene, acetoacetyl fluoride, acetoacetyl chloride, acetoacetic acid, or an isopropenyl ester of the formula $CH_2=C(OOCR)-CH_3$ (III) in which R represents an alkyl radical having from 1 to 4 carbon atoms, or an optionally substituted phenyl or benzyl radical.

Owing to the fact that the ester group of the compounds of formula III is eliminated during the course of the reaction the nature of R is of minor importance. Compounds in which R stands for $CH_3$ are preferred. The reaction temperature varies in accordance with the reaction components used, in general it is in the range of from −10° to +60° C, preferably 0° to 45° C.

To carry out the process of the invention one of the reaction components is first introduced into the reaction vessel and the other one is added at the reaction temperature while stirring or both reaction components are introduced into the reaction vessel, preferably at the same rate.

Especially good results are obtained with the use of an inert solvent or diluent as reaction medium and/or as solvent for the reaction component(s).

Suitable solvents or diluents are, for example, aliphatic or aromatic hydrocarbons such as pentane, hexane, cyclohexane, gasoline, petroleum ether, benzene, toluene, xylene; or halohydrocarbons such as methylene chloride, chloroform, carbon tetrachloride; ethers such as diethyl ether, di-isopropyl ether, dimethoxyethane, tetra-hydrofurane, dioxane; or nitriles such as acetonitrile or propionitrile, or mixtures of the aforesaid solvents, and $SO_2$. Preferred solvents are methylene chloride, chloroforme, and carbon tetrachloride. With the use of the latter solvent the reaction product separates as the heavier phase and can be freed of the major portion of the solvent by simple decantation. Inert solvents the boiling point of which is within the desired temperature range are preferred.

The amount of inert solvent used is not critical and depends or the practical requirements in each case. In general, the solvent is used in an about 1 to 20 fold excess, calculated on the amount of reaction components. Smaller or larger amounts are likewise possible, the upper limit being determined by economical reasons.

The progress of the reaction can be readily controlled by IR spectroscopic analysis by the disappearance of the characteristic isocyanate band of the FSI or CSI at 4.4 $\mu$ and of the diketene bands at 5.2 and 5.3 $\mu$ and by the formation of three characteristic bands of the compound of formula I at 5.6, 5.8 and 6.03 $\mu$.

To obtain the reaction product the solvent is distilled off under reduced pressure or separated by decantation from the precipitated mostly crystallin crude product. The reaction product may be further purified according to known methods, for example by recrystallization.

More particularly, the reaction according to the invention proceeds as follows:

1. with the use of diketene preferably at a temperature of from −10° to +60° C, more preferably +20° to +55° C according to the following reaction scheme:

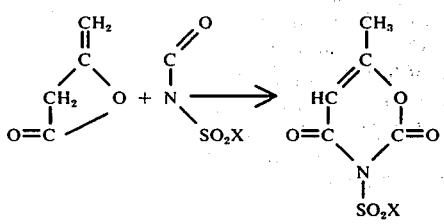

with approximately equimolecular amounts or optionally a small excess of up to 10 % of one of the reaction components;

2. with the use of acetoacetyl chloride, which is preferably prepared from diketene by reacting it with hydrogen chloride (cf. J.Am.Chem.Soc. volume 62 (1940), page 1548 or German Offenlegungsschrift 1,931,964), preferably at a temperature of from −20° to +60° C, more preferably −10° to +30° C according to the following reaction scheme

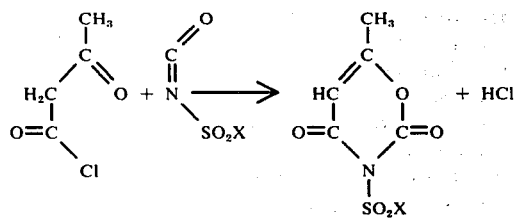

with approximately equimolecular amounts or optionally a small excess of one of the reaction components as sub 1). The same applies to the use of acetoacetyl fluoride;

3. with the use of acetoacetic acid preferably at a temperature of from −35° to +40° C, more preferably −20° to +20° C according to the following reaction scheme

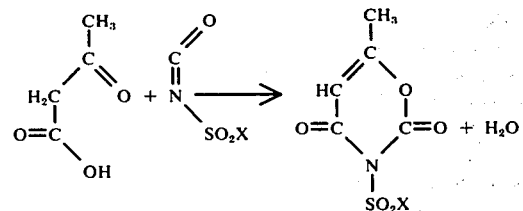

Owing to the fact that the water formed in the condensation reacts with a second molecule FSI or CSI two moles of FSI or CSI are preferred or a slight excess of up to 10 % per mole of acetoacetic acid. The $CO_2$ formed may serve to control the reaction;

4. with the use of isopropenyl esters preferably at a temperature of from −30° to +40° C, more preferably −20° to +20° C according to the following reaction scheme

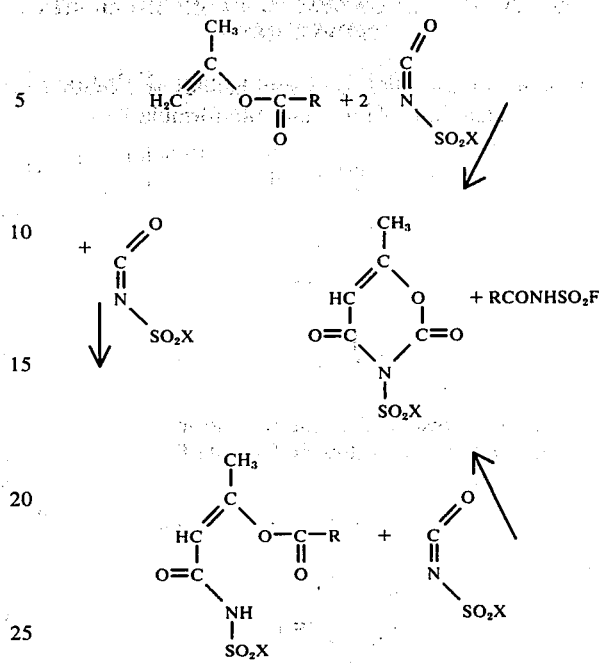

The latter reaction can thus be carried out in one or two stages, for example with R being $CH_3$ as follows:

a. from isopropenyl acetate and 1 mole FSI or CSI there is obtained, at a reaction temperature of from −40° to +20° C, preferably −30° to +10° C, besides compound I, β-acetoxycrotonic acid amide-N-sulfohalide which can be isolated;

b. from β-acetoxy-crotonic acid amide-N-sulfohalide there is obtained with a further mole FSI or CSI, preferably at a slightly elevated temperature of up to +30° C, the desired compound I besides acetamide-N-sulfohalide.

This reaction is, however, preferably carried out in one stage without isolation of intermediate products, preferably at a temperature of from −20° to +30° C, more preferably −10° to +20° C with 2 moles FSI or CSI per mole of isopropenyl ester or a slight excess of one of the former compounds of up to 10 %. The sparingly soluble acetamide-N-sulfohalide can be first separated in crystal form and then the desired compound I is obtained, for example by concentration of the solvent or addition of $CCl_4$, which may be further purified by known methods, for example by recrystallization.

Although the reaction mechanism of the process of the invention is not yet clarified in detail it can be assumed that the reactions 1 − 4 listed above take place according to the same principle, so that reactions 1 − 3 also proceed via the enol grouping as in the case of reaction 4 and formally the following reaction scheme is valid for all 4 reactions:

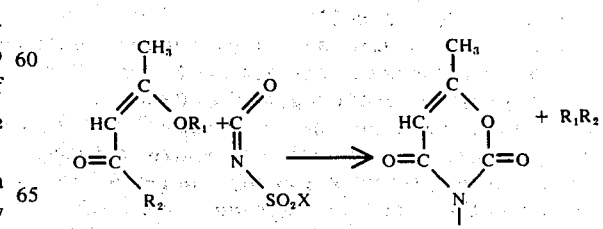

in which for reactions 2 and 3: $R_1$ is hydrogen and $R_2$ is chlorine or hydroxy, for reaction 1: $R_1$-$R_2$ is a direct linkage and for reaction 4: $R_1$ is

and $R_2$ is —NHSO$_2$X

Intermediate stages which can be assumed in this formal reaction scheme could not be isolated so far.

In contradistinction to the aforesaid 3-alkyl- and 3-aryl-substituted 6-methyl-2H-1,3-oxazin-2,4(3H)-diones or the methyl compound of formula II unsubstituted in 3-position (R = H), the novel compounds of formula I are very sensitive compounds which start to decompose above their melting point at a temperature below 100° C. Moreover, they are very sensitive to hydrolysis, above all the 3-chlorosulfonyl compound which is readily hydrolized to the 6-methyl-2H-1,3-oxazin-2,4-(3H)dione (compound of formula II with R = H), while compound I with X = fluorine yields with water acetoacetamide-N-sulfofluoride.

The compounds of the invention, especially the fluorine derivative of compound I are suitable as intermediate products for the manufacture of 6-methyl-3,4-dihydro-1,2,3-oxathiazin-4-one-2,2-dioxide and its non toxic salts (cf. Application Ser. No. P 2434562.8 filed concurrently herewith) which are distinguished by a very sweet taste (Cf. U.S. Pat. No. 3,689,486). These compounds can be prepared from compound I by a treatment with aqueous alkali in one stage. From the chlorosulfonyl derivative there can be obtained the known 6-methyl-2H-1,3-oxazin-2,4(3H)-dione (compound II, R=H) and other N-substituted derivatives. By a reaction with NH$_3$ or amines the compounds of the invention yield known uraciles having a herbicidal effect (cf. U.S. Pat. Nos. 3,235,360, 3,235,361, 3,235,362 and Germ. Pat. No. 1,240,698).

The following examples illustrate the invention.

EXAMPLE 1

6-Methyl-2H-1,3-oxazin-2,4-(3H)-dione-3-sulfofluoride 42 g diketene (0.5 mole) were added dropwise while stirring to a solution of 40° – 60° C of 62.5 g (0.5 mole) FSI in 100 ml CCl$_4$. After the addition of about 10 ml diketene an exothermal reaction started, the reaction mixture acquired a dark color and a heavy second phase was formed. After subsiding of the reaction, stirring was continued for a further 20 minutes at 60° C and the mixture was allowed to cool. The lower dark phase solidified in the form of crystals so that the upper phase of CCl$_4$ could be decanted. After recrystallization of the crystal magma from propylene chloride 68 g of slightly colored crystals of 6-methyl-2H-1,3-oxazin-2,4-(3H)-dione-3-sulfofluoride melting at 80° – 83° C were obtained.

Yield 65% of theory.

Analysis: C$_5$H$_4$FNO$_5$S m.w. 209.2; calc.: C 28.7% H 1.9% F 9.1% N 6.7% S 15.3%; found: C 29.0% H 2.0% F 9.4% N 6.8% S 15.4%.

molecular weight (mass/spectrum): 209

IR (KBr): 5.5 5.7 5.94 6.8 7.5 8.1 8.35 μ

$^1$H-NMR(CD$_3$CN): δ = 2.2 (d, J = 1 Hz) and 6.0 ppm (q, J = 1 Hz)

EXAMPLE 2

From two separate dropping funnels 62.5 g (0.5 mole) FSI and 42 g (0.5 mole) diketene were added simultaneously to 100 ml CHCl$_3$ boiling with reflux at a rate that equimolecular amounts were added per unit of time. The solution remained homogeneous and boiled by itself owing to the reaction heat. After evaporation of the solvent, the residue remaining behind was worked up as described in Example 1. Properties, analysis and spectra of the product were the same as in Example 1.

Yield 62% of theory.

The same result was obtained with methylene chloride as solvent.

EXAMPLE 3

6-Methyl-2H-1,3-oxazin-2,4-(3H)dione-3-sulfochloride 42 g (0.5 mole) diketene were added dropwise to a solution boiling with reflux of 71 g (0.5 mole) CSI at a rate such that the solution continued to boil. After subsiding of the reaction, the mixture was refluxed for a further 20 minutes and the solvent was evaporated. A black sirupy mass was obtained from which 68.8 g colorless crystalline 6-methyl-2H-1,3-oxazin-2,4-(3H)-dione-3-sulfochloride melting at 85° C were obtained by extraction with diethyl ether or propyl chloride.

Yield 61% of theory.

Analysis: C$_5$H$_4$ClNO$_5$S m.w. 225.6; calc.: C 26.6% H 1.8% Cl 15.7%; found: C 26.8% H 1.8% Cl 15.5%.

IR(KBr): 5.5 5.7 5.92 6.95 7.5 8.3 μ

$^1$H-NMR(CD$_3$CN): δ = 2.2 (d, J = 1 Hz) and 6.0 ppm (q, J = 1 Hz)

EXAMPLE 4

6-Methyl-2H-1,3-oxazin-2,4-(3H)-dione-3-sulfofluoride from diketene and HCl in CHCl$_3$ 36.5 g hydrogen chloride (1.0 mole) were introduced over a period of 2 hours, while stirring at −20° C, into a solution of 84 g (1.0 mole) distilled diketene in 400 ml dry chloroform. Stirring was continued for a further 30 minutes and then 80 ml FSI (1.0 mole) were added dropwise over a period of 30 minutes at −20° to −5° C. The reaction mixture was allowed to stand for 1 hour at 0° C, the solvent was distilled off under reduced pressure and the yellow oil obtained was taken up in isopropyl ether. 74 g of colorless crystals of 6-methyl-2H-1,3-oxazin-2,4-(3H)-dione-3-sulfofluoride separated. After recrystallization from propyl chloride, the product melted at 85° – 86° C.

Yield 35% of theory.

The properties, analysis and spectra were identical with those of the product of Example 1.

EXAMPLE 5

6-Methyl-2H-1,3-oxazin-2,4-(3H)-dione-3-sulfofluoride from diketene and HCl (acetoacetic acid chloride) in CH$_2$Cl$_2$/isopropyl ether Under the conditions of Example 4 acetoacetyl chloride was prepared from 84 g diketene (1.0 mole) and 36.5 g hydrogen chloride (1.0 mole) in 100 ml dry methylene chloride and isolated by substantially distilling off the methylene chloride at −20° C under reduced pressure. The reaction product was taken up in 300 ml isopropyl ether while cooling and at −20° C 80 ml FSI (1.0 mole) were added dropwise. The reaction mixture was allowed to stand overnight at −20° C whereupon the separated colorless crystals of 6-methyl-2H-1,3-oxazin-2,4-(3H)-dione-3-sulfofluoride melting at 85° − 86° C were filtered off with suction.

Yield 42% of theory.

The properties, analysis and spectra were identical with those of the product of Example 1.

EXAMPLE 6

Under the conditions of Example 4 acetoacetyl chloride was prepared at −20° C by introducing 18.3 g (0.5 mole) gaseous HCl into 42 g (0.5 mole) diketene in 100 ml distilled $CH_2Cl_2$, 62.5 g (0.5 mole) FSI were added and the reaction mixture was abandoned for 24 hours at −20° C and for 6 hours at room temperature. After evaporation of the solvent under reduced pressure, a residue solidifying in crystal form remained behind, from which, after extraction with diethyl ether and recrystallization, 62 g of still yellowish crystals of 6-methyl-2H-1,3-oxazin-2,4-(3H)-dione-3-sulfofluoride melting at 81° − 84° C were obtained.

Yield 59% of theory.

Analysis, properties and spectra were identical with those of the product of Example 1.

EXAMPLE 7

To prepare acetoacetyl chloride 18.3 g (0.5 mole) gaseous HCl were introduced over a period of 3 hours at −30° C into a solution of 42 g (0.5 mole) diketene in 150 ml distilled $CHCl_3$. 62.5 g (0.5 mole) FSI were added dropwise while raising the temperature slowly to the boiling point of $CHCl_3$ by external heating and the mixture was kept at said temperature for 20 minutes. After evaporation of the solvent under reduced pressure, a dark oil was obtained from which 66 g yellow-brown crystals of 6-methyl-2H-1,3-oxazin-2,4(3H)-dione-3-sulfofluoride separated on stirring with di-isopropyl ether. The crystals recrystallized from propyl chloride melted at 82° − 86° C.

Yield 63% of theory.

Analysis, properties and spectra were identical with those of the product of Example 1.

EXAMPLE 8

18.3 (0.5 mole) gaseous HCl were introduced over a period of 3 hours at −30° C into a solution of 42 g (0.5 mole) diketene in 150 ml liquid $SO_2$. After addition of 62.5 g (0.5 mole) FSI the solution was refluxed for 25 hours (−6° to −8° C). The oily residue obtained after evaporation of the $SO_2$ crystallized on stirring with di-isopropyl ether and 44 g of colorless crystals of 6-methyl-2H-1,3-oxazin-2,4-(3H)-dione-3-sulfofluoride melting at 85° − 86° C were obtained.

Yield 42% of theory.

Analysis, properties and spectra were identical with those of the product of Example 1.

EXAMPLE 9

18.3 g (0.5 mole) gaseous HCl were introduced over a period of 30 minutes at −20° C into a solution of 42 g (0.5 mole) diketene in 250 ml $CCl_4$. Immediately thereafter, 62.5 g (0.5 mole) FSI were added and the temperature of the mixture was allowed to rise to room temperature while stirring. During the course of 5 to 6 hours a heavy phase formed which partially crystallized on standing. After decantation of the supernatant solvent the residue was treated with di-isopropyl ether. 60 g of yellowish crystals of 6-methyl-2H-1,3-oxazin-2,4-(3H)-dione-3-sulfofluoride melting at 82° − 85° C were obtained.

Yield 57% of theory.

Analysis, properties and spectra were identical with those of the product of Example 1.

EXAMPLE 10

6-Methyl-2H-1,3-oxazin-2,4-(3H)-dione-3-sulfofluoride from crystalline acetoacetic acid + 2 moles FSI in $CH_2Cl_2$ A solution cooled to 0° C of 42.5 g (0.415 mole) acetoacetic acid in 200 ml methylene chloride was added dropwise over a period of 2 hours to a mixture likewise cooled to 0° C of 70.0 ml (0.87 mole) FSI and 50 ml dry methylene chloride. During the reaction 7.8 l $CO_2$ were split off. The methylene chloride was distilled off under reduced pressure and the remaining oil was rubbed with isopropyl ether. 64.0 g of colorless crystals of 6-methyl-2H-1,3-oxazin-2,4-(3H)-dione-3-sulfofluoride melting at 84° −86° C were obtained.

Yield 74% of theory.

Properties, analysis and spectra were identical with those of the product of Example 1.

EXAMPLE 11

6-Methyl-2H-1,3-oxazin-2,4-(3H)-dione-3-sulfochloride 18.3 g (0.5 mole) gaseous HCl were introduced at −20° C into a solution of 42 g (0.5 mole) diketene in 100 ml $CH_2Cl_2$ and 70.8 g (0.5 mole) CSI were added to the acetoacetyl chloride. The solution was kept for 3 days at −20° C to −30° C, then for 3 days at 0° C. After evaporation of the solvent under reduced pressure a dark sirupy mass was obtained from which, by extraction with ether and recrystallization, 50 g of slightly yellowish crystals of 6-methyl-2H-1,3-oxazin-2,4-(3H)-dione-3-sulfochloride melting from 82° C onward could be obtained.

Yield 44% of theory.

Properties, analysis and spectra were identical with those of the product of Example 3.

EXAMPLE 12

6-Methyl-2H-1,3-oxazin-2,4-(3H)-dione-3-sulfochloride

A cold solution of 59 g (0.58 mole) crystalline acetoacetic acid in 200 ml methylene chloride was added dropwise at 0° C to a mixture of 102 ml (1.17 moles) chlorosulfonyl isocyanate and 100 ml dry methylene chloride. During the course of 2 hours 0.56 mole gaseous $CO_2$ escaped. The methylene chloride was then distilled off under reduced pressure and the oily residue was rubbed with 500 ml isopropyl ether whereby it crystallized.

95 g (0.42 mole) 6-methyl-2H-1,3-oxazin-2,4-(3H)-dione-3-sulfochloride melting at 86° C (recrystallized from propyl ether) were obtained, corresponding to 72% of the theory.

Analysis and spectra were identical with those of the product of Example 3.

EXAMPLE 13

6-Methyl-2H-1,3-oxazin-2,4-(3H)-dione-3-sulfofluoride 125 g (1 mole) FSI were added dropwise at −20° C to a solution of 120 g (0.2 mole) isopropenyl acetate in 200 g diisopropyl ether. After standing for 3 days at −20° C the crystallized β-acetoxy-crotonic acid amide-N-sulfofluoride was filtered off with suction and dried under reduced pressure.

12.5 g FSI (0.1 mole) were added dropwise at 0° C to a solution of 22.5 g (0.1 mole) of the N-sulfochloride obtained in 50 ml anhydrous ethyl acetate. After 60 hours the solvent was evaporated and the crystalline residue was stirred as rapidly as possible with $NaHCO_3$ solution and ice and the separating crystals were filtered off with suction. They were recrystallized from $CHCl_3/CCl_4$. 8 g 6-methyl-2H-1,3-oxazin-2,4-(3H)-dione-3-sulfofluoride melting form 75° C onward were obtained.

Yield 38% of theory.

Properties, analysis and spectra were identical with those of the product of Example 1.

EXAMPLE 14

20 g (0.2 mole) isopropenyl acetate were added dropwise at 20° C to a solution of 50 g (0.4 mole) FSI in 50 ml $CHCl_3$. After 15 minutes the solution was cooled to −10° C, the acetamide-N-sulfofluoride crystallized out and was filtered off with suction. $CCl_4$ was then added to the filtrate until it became turbid and the mixture was cooled to −20° C. By suction filtration 20 g of crystalline 6-methyl-2H-1,3-oxazin-2,4-(3H)-dione-3-sulfofluoride was isolated.

Yield 48% of theory.

Properties, analysis and spectra were identical with those of the product of Example 1.

What is claimed is:

1. A 3-sulfohalide of 6-methyl-2H-1,3-oxazin-2,4(3H)-dione of the formula

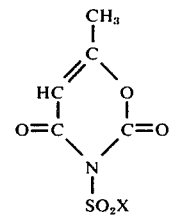

in which X represents fluorine or chlorine.

2. The sulfohalide defined in claim 1 in which X is fluorine.

3. The sulfohalide defined in claim 1 in which X is chlorine.

* * * * *